United States Patent

Sunagawa et al.

Patent Number: 5,578,722
Date of Patent: Nov. 26, 1996

[54] PROCESS FOR PREPARING CARBAPENEM COMPOUNDS

[75] Inventors: Makoto Sunagawa, Itami; Haruki Matsumura, Nara, both of Japan

[73] Assignee: Sumitomo Pharmaceuticals Co., Ltd., Osaka-fu, Japan

[21] Appl. No.: 407,071

[22] Filed: Mar. 20, 1995

[30] Foreign Application Priority Data

Mar. 29, 1994 [JP] Japan .................................. 6-083928

[51] Int. Cl.⁶ .................................................. C07D 487/04
[52] U.S. Cl. .......................................... 540/302; 540/350
[58] Field of Search ................................. 540/302, 350

[56] References Cited

U.S. PATENT DOCUMENTS

| | | | |
|---|---|---|---|
| 4,350,631 | 9/1982 | Christensen et al. | 540/302 |
| 5,310,897 | 5/1994 | Sunagawa et al. | 540/302 |

OTHER PUBLICATIONS

J. Org. Chem., 53, 4154–4156 (1988).
Deziel et al., Tetrahedron Letters, 30, 1345–1348 (1989).
Sunagawa et al., Chem. Pharm. Bull, 42 (7) 1381–1387 (1994).

*Primary Examiner*—Rebecca Cook
*Attorney, Agent, or Firm*—Birch, Stewart, Kolasch & Birch, LLP

[57] ABSTRACT

Novel and effective process for preparing a carbapenem compound of the formula (III):

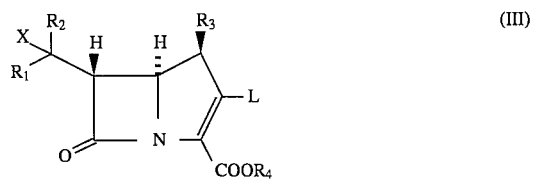

wherein $R_1$ and $R_2$ are each H or lower alkyl, $R_3$ is lower alkyl, $R_4$ is a protecting group, L is substituted or unsubstituted arylsulfonyloxy, lower alkanesulfonyloxy, halogeno-lower alkanesulfonyloxy, di-lower alkylphosphoryloxy, etc., and X is H or protected hydroxy, which comprises reacting a β-lactam compound (I) with an acetic acid ester derivative (II), in the presence of base, followed by treating the product with an active esterifying agent for a hydroxy group, said compound (III) being useful as intermediate in preparing 1β-alkylcarbapenem compounds having antibacterial activity.

10 Claims, No Drawings

PROCESS FOR PREPARING CARBAPENEM COMPOUNDS

FIELD OF INVENTION

The present invention relates to a novel process for preparing carbapenem compounds.

PRIOR ART

Since thienamycin was found from natural resources and was reported to have a potent antibacterial activity with a broad antibacterial spectrum [cf. J. Am. Chem. Soc., 100, 313 (1978)], there have been reported various useful carbapenem compounds as an antibacterial agent. For example, it has been known that a carbapenem compound wherein the methylene group at 1-position of the carbapenem nucleus has alkyl substituents, especially a 1β-methylcarbapenem compound, is excellently stable against the renal enzyme, i.e. dehydropeptidase-I and hence is quite useful as an antibacterial agent [cf. Heterocycles, 21, 29 (1984)]. (The numbering of the positions of the carbapenem nucleus in the literature is conventional one as shown in the following formula (A), and the 1-position of the formula (A) corresponds to the 4-position according to the nomenclature in the present invention)

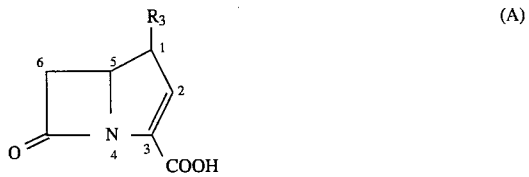

(A)

Since then, attention has been paid to develop a useful and excellent process for preparing 1β-alkylcarbapenem compounds.

In this respect, it is also known that the carbapenem compounds of the formula (III) as shown hereinbelow are an important intermediate for preparing 1β-alkylcarbapenem compounds. Accordingly, many researchers have tried various processes for preparing said carbapenem compounds (III) to find the most effective process. Among them, the process disclosed in U.S. Pat. No. 5,310,897 wherein the cyclization reaction and phosphorization reaction are carried out in one-pot system without isomerization of the 1β-alkyl group, is simple in the procedure and is suitable for the production of the desired carbapenem compounds (III) on an industrial scale.

It has been, however, still desired to develop a process more suitable for the production of the desired carbapenem compounds (III) on a larger scale.

The present inventors have intensively studied to develop a novel and effective process for preparing the carbapenem compounds by modifying the process known to be suitable for the industrial production of said compounds wherein the cyclization reaction and phosphorization reaction are carried out in one-pot system, and have found that the object can be achieved by reacting a specific β-lactam compound with a specific acetic acid ester derivative in the presence of a base, followed by treating with an active esterifying agent.

BRIEF DESCRIPTION OF INVENTION

An object of the present invention is to provide an improved process for preparing the carbapenem compounds being useful as an intermediate for the 1β-alkylcarbapenem compounds. Another object of the present invention is to provide a process for preparing the desired carbapenem compounds on a large scale. A further object of the present invention is to provide a process for preparing the desired carbapenem compounds in a high yield without epimerization.

DETAILED DESCRIPTION OF INVENTION

The present invention relates to a novel process for preparing a carbapenem compound of the formula (III):

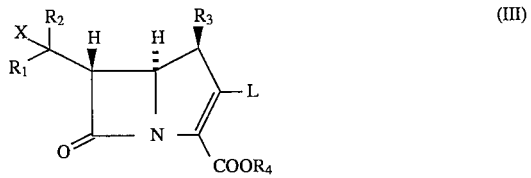

(III)

wherein $R_1$ and $R_2$ are the same or different and each a hydrogen atom or a lower alkyl group, $R_3$ is a lower alkyl group, $R_4$ is a protecting group for a carboxyl group, L is a substituted or unsubstituted arylsulfonyloxy group, a lower alkanesulfonyloxy group, a halogeno-lower alkanesulfonyloxy group, a di-lower alkylphosphoryloxy group, a di-(halogeno-lower alkyl)phosphoryloxy group or a di-(substituted or unsubstituted aryl)phosphoryloxy group, and X is hydrogen atom or a protected hydroxy group, which comprises reacting a β-lactam compound of the formula (I):

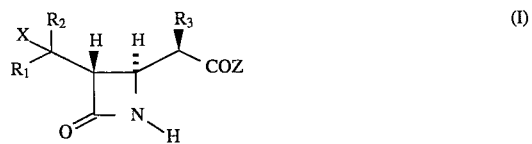

(I)

wherein $R_1$, $R_2$, $R_3$, X are the same as defined above, and COZ is an active ester of a carboxyl group, a substituted or unsubstituted arylthiocarbonyl group, a substituted or unsubstituted heteroarylthiocarbonyl group, a substituted or unsubstituted aralkylthiocarbonyl group, a substituted aryloxycarbonyl group, or a heteroaryloxycarbonyl group, with an acetic acid ester derivative of the formula (II):

(II)

wherein Y is an active ester of a hydroxy group or a halogen atom and $R_4$ is the same as defined above, in the presence of a base, followed by treating the product with an active esterifying agent for a hydroxy group. Said carbapenem compound (III) is an important intermediate in preparing 1β-alkylcarbapenem compounds that are useful as antibacterial agents. The process of the present invention is more efficient than the conventional processes for preparing the carbapenem compounds (III).

Each group of the present invention represents especially the following groups.

The lower alkyl group includes, for example, an alkyl group having 1 to 4 carbon atoms such as methyl group, ethyl group, n-propyl group, n-butyl group, etc.

The protecting group present in the protected hydroxy group represented by X may be any conventional protecting group for hydroxy groups, for example, an alkoxycarbonyl group having 1 to 4 carbon atoms in the alkoxy moiety (e.g. t-butyloxycarbonyl group); a halogenoalkyloxycarbonyl group having 1 to 4 carbon atom in the alkyl moiety (e.g. 2-iodoethyloxycarbonyl group, 2,2,2-trichloroethyloxycarbonyl group); an alkenyloxycarbonyl group having 3 to 5 carbon atoms in the alkenyloxy moiety (e.g. allyloxycarbonyl group); a substituted or unsubstituted aralkyloxycarbonyl group (e.g. benzyloxycarbonyl group, o-nitrobenzyloxycarbonyl group, p-nitrobenzyloxycarbonyl group, p-methoxybenzyloxycarbonyl group); a tri-alkylsilyl group having 1 to 4 carbon atoms in the alkyl moiety (e.g. trimethylsilyl group, triethylsilyl group, t-butyldimethylsilyl group); a di-arylalkylsilyl group having 1 to 4 carbon atoms in the alkyl moiety (e.g. t-butyldiphenylsilyl group); a substituted methyl group (e.g. methoxymethyl group, 2-methoxyethoxymethyl group, methylthiomethyl group); tetrahydropyranyl group, and the like. The preferable protecting group for the hydroxy group is a tri-alkylsilyl group having 1 to 4 carbon atoms in the alkyl moiety, a di-arylalkylsilyl group having 1 to 4 carbon atoms in the alkyl moiety, a substituted methyl group, tetrahydropyranyl group, and the like.

When COZ is an active ester of a carboxyl group, Z includes, for example, a heteroaryl group (e.g. imidazole group, triazole group), a cyclic imidoxy group (e.g. N-succinimidoxy group, N-phthalimidoxy group, benzotriazolyloxy group), a heterocycloalkyl group (e.g. 3-(2-thioxo)thiazolidinyl group), and the like.

When COZ is a substituted or unsubstituted arylthiocarbonyl group, the substituted or unsubstituted aryl moiety includes, for example, phenyl group, a phenyl group substituted by 1 to 3 halogen atoms such as chlorine, bromine, iodine, p- or o-nitrophenyl group, p-methoxyphenyl group, and the like.

When COZ is a substituted or unsubstituted heteroarylthiocarbonyl group, the substituted or unsubstituted heteroaryl moiety includes, for example, 2-, 3- or 4-pyridyl group, 2-pyrimidyl group, 2-(4,6-dimethyl)pyrimidyl group, and the like.

When COZ is a substituted or unsubstituted aralkylthiocarbonyl group, the substituted or unsubstituted aralkyl moiety includes, for example, a substituted or unsubstituted mono-arylalkyl group such as benzyl group, p-methoxybenzyl group, 2,4-dimethoxybenzyl group, p- or o-nitrobenzyl group, p-chlorobenzyl group, and the like.

When COZ is a substituted aryloxycarbonyl group, the substituted aryloxy moiety includes, for example, p- or o-nitrophenyloxy group, 2,4-dinitrophenyloxy group, a phenyloxy group substituted by 1 to 3 halogen atoms selected from chlorine, bromine, iodine, etc., and the like.

When COZ is a heteroaryloxycarbonyl group, the heteroaryloxy moiety includes, for example, 2-, 3- or 4-pyridyloxy group, and the like.

The preferable one is, for example, an active ester of a carboxyl group, a substituted or unsubstituted arylthiocarbonyl group, a substituted or unsubstituted heteroarylthiocarbonyl group, and the like.

The protecting group for a carboxyl group represented by $R_4$ in the acetic acid ester derivative of the formula (II) may be any conventional one, but preferably a lower alkyl group having 1 to 4 carbon atoms such as methyl group, ethyl group, isopropyl group, t-butyl group, etc.; a halogeno-lower alkyl group having 1 to 4 carbon atoms such as 2-iodoethyl group, 2,2,2-trichloroethyl group, etc.; a methyl group substituted by a lower alkoxy group having 1 to 4 carbon atoms such as methoxymethyl group, ethoxymethyl group, isobutoxymethyl group, etc.; a methyl group substituted by a lower aliphatic acyloxy group having 2 to 5 carbon atoms such as acetoxymethyl group, propionyloxymethyl group, butyryloxymethyl group, pivaloyloxymethyl group, etc.; a substituted or unsubstituted lower alkenyl group having 3 to 10 carbon atoms such as allyl group, 2-methylallyl group, 3-methylallyl group, 3-phenylallyl group, etc.; a substituted or unsubstituted mono-arylalkyl group such as benzyl group, p- or o-nitrobenzyl group, p-chlorobenzyl group, and the like.

The active ester of a hydroxy group represented by Y includes, for example, a substituted or unsubstituted arylsulfonyloxy group such as benzenesulfonyloxy group, p-toluenesulfonyloxy group, p-nitrobenzenesulfonyloxy group, p-bromobenzenesulfonyloxy group, etc.; a lower alkanesulfonyloxy group having 1 to 4 carbon atoms such as methanesulfonyloxy group, ethanesulfonyloxy group, etc.; a halogeno-lower alkanesulfonyloxy group having 1 to 4 carbon atoms such as trifluoromethanesulfonyloxy group, etc. The halogen atom represented by Y includes chlorine, bromine, iodine, etc. The preferable Y group is a halogen atom.

The process of the present invention is illustrated in the following Reaction Scheme-I.

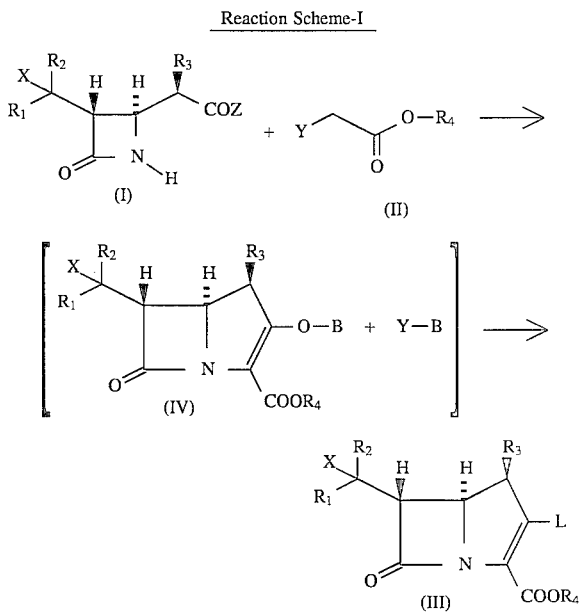

wherein $R_1$, $R_2$, $R_3$, $R_4$, X, Y, Z and L are the same as defined above, and B is an alkali metal.

The carbapenem compound of the formula (III) is prepared by reacting the compound (I) with the acetic acid ester derivative (II) in the presence of a base in an inert solvent, followed by treating the product with an active esterifying agent for hydroxy group. In the above reaction, the second step, i.e. the treatment with the active esterifying agent is carried out without isolating the product (IV) obtained in the former reaction.

In the compound (III), L means an ester group produced by the reaction of hydroxy group and an active esterifying agent for hydroxy group. For example, the substituted or unsubstituted arylsulfonic acid ester (i.e. a substituted or unsubstituted arylsulfonyloxy group) represented by L includes, for example, benzenesulfonic acid ester, p-toluenesulfonic acid ester, p-nitrobenzenesulfonic acid ester, p-bromobenzenesulfonic acid ester, etc. The lower alkanesulfonic acid ester (i.e. a lower alkanesulfonyloxy group) includes, for example, methanesulfonic acid ester, ethanesulfonic acid ester, etc. The halogeno-lower alkanesulfonic acid ester (i.e. a halogeno-lower alkanesulfonyloxy group) includes, for example, trifluoromethanesulfonic acid ester, etc. The dilower alkylphosphoric acid ester (i.e. a di-lower alkylphosphoryloxy group) includes, for example, dimethylphosphoric acid ester, diethylphosphoric acid ester, etc. The di-halogeno-lower alkylphosphoric acid ester (i.e. a di(halogeno-lower alkyl)phosphoryloxy group) includes, for example, di(trichloroethyl)phosphoric acid ester, etc., and the di(substituted or unsubstituted aryl)phosphoric acid ester (i.e. di(substituted or unsubstituted aryl)phosphoryloxy group) includes, for example, diphenylphosphoric acid ester, di-p-chlorophenylphosphoric acid ester, ditolylphosphoric acid ester, etc.

Among these active esters groups for L, the preferable one is p-toluenesulfonic acid ester, methanesulfonic acid ester, diphenylphosphoric acid esters, etc.

Thus, the active esterifying agent for hydroxy group is a reagent which reacts with the compound (IV) to give the above-mentioned active ester groups.

The active esterifying agent used in the present invention is, for example, benzenesulfonyl chloride, p-toluenesulfonyl chloride, p-toluenesulfonic anhydride, p-nitrobenzenesulfonyl chloride, p-bromobenzenesulfonyl chloride, methanesulfonyl chloride, ethanesulfonyl chloride, trifluoromethanesulfonyl chloride, methanesulfonic anhydride, trifluoromethanesulfonic anhydride, dimethyl chlorophosphate, diethyl chlorophosphate, di(trichloroethyl) chlorophosphate, diphenyl chlorophosphate, di-p-chlorophenyl chlorophosphate, ditolyl chlorophosphate, etc.

The alkali metal is, for example, lithium, sodium, potassium, etc.

The inert solvent may be any one which does not affect the reaction, but the preferable inert solvent is, for example, ethers (e.g. diethyl ether, tetrahydrofuran, dioxane, ethylene glycol dimethyl ether, etc.), aromatic hydrocarbons (e.g. benzene, toluene, monochlorobenzene, etc.), acetonitrile, dimethylformamide, dimethyl sulfoxide, hexamethylphosphoric triamide (HMPT), t-butanol, or a mixture thereof.

The acetic acid ester derivative (II) is used in an amount sufficient for proceeding the reaction, for example, in an amount of 2 to 4 moles to 1 mole of the compound (I).

The base used in the reaction of the compound (I) and the acetic acid ester derivative (II) is, for example, an alkali metal salt with an amine compound such as lithium diisopropylamide, lithium bis(trimethylsilyl)amide, sodium bis(trimethylsilyl)amide, potassium (trimethylsilyl)amide, sodium amide, etc., an alkali metal salt with an alcohol such as potassium t-butoxide, etc., an alkali metal hydride such as sodium hydride, potassium hydride, etc., n-butyl lithium, sodium methylsulfinylmethide, and the like. Among these bases, the preferable one is sodium hydride.

The base is used in an amount sufficient for proceeding the reaction, for example, in an amount of 2 to 5 moles to 1 mole of the compound (I). The reaction may be controlled by cooling or heating the reaction mixture, but it is preferably carried out at a temperature from −78° C. to 10° C.

If necessary, it may be added a catalytic amount of water or an alcohol into the reaction system in order to promote the reaction.

The active esterifying agent in the active esterification reaction of hydroxy group is used in an amount sufficient for proceeding the reaction, for example, in an amount of 1 to 2.5 moles to 1 mole of the compound (I). The reaction may be controlled by cooling or heating the reaction mixture, but the reaction is usually carried out at a temperature from −78° C. to 60° C., more preferably at a temperature from −40° C. to 10° C.

Besides, after the reaction is complete, the obtained product can be isolated by a conventional method in the organic chemistry.

The enolate salt (IV) obtained by reacting the compound (I) with the acetic acid ester derivative (II) in the presence of a base in an inert solvent retains its stereochemical structure based on the asymmetric carbon atom (5-position) of the starting compound (I) under conditions for its preparation, i.e. under basic conditions, so that the compound (IV) is converted into the compound (III) while retaining the stereochemical structure of the alkyl group represented by $R_3$ on the starting compound (I). That is, according to the present invention, the carbapenem compound (III) is obtained without epimerization.

In this case, the enolate compound (IV) may exist in the form of a chelate structure as follows.

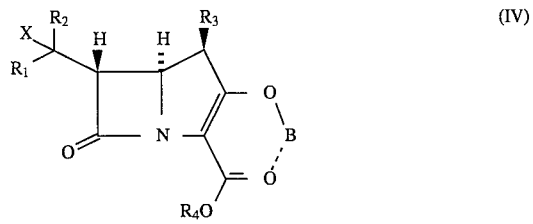

Besides, in the process of the present invention, a residue represented by Z is released in the reaction system by the reaction of the compound (I) with the compound (II). When the released residue Z remains in the reaction system, it may affect the subsequent reaction with the active esterifying agent of hydroxy group. However, even in this case, the acetic acid ester derivative (II) used in this reaction can capture the residue Z so that the effect of the residue Z on the subsequent reaction is prevented.

The starting compound (I) may be prepared by the method disclosed in U.S. Pat. No. 5,310,897.

The representative examples of the β-lactam compound of the formula (I) are shown as below.

(1) (3S,4S)-3-[(1R)-1-t-Butyldimethylsilyloxyethyl]-4-[(1R)-1-imidazolylcarbonylethyl]-2-azetidinone (2) (3S,4S)-3-[(1R)-1-t-Butyldimethylsilyloxyethyl]-4-[(1R)-1-triazolylcarbonylethyl]-2-azetidinone (3) (3S,4S)-3-[(1R)-1-t-Butyldimethylsilyloxyethyl]-4-[(1R)-1-(N-succinimidoxy)carbonylethyl]-2-azetidinone (4) (3S,4S)-3-[(1R)-1-t-Butyldimethylsilyloxyethyl]-4-[(1R)-1-(N-phthalimidoxy)carbonylethyl]-2-azetidinone (5) (3S,4S)-3-[(1R)-1-t-Butyldimethylsilyloxyethyl]-4-[(1R)-1-(1benzotriazolyloxy)carbonylethyl]-2-azetidinone (6) (3S,4S)-3-[(1R)-1-t-Butyldimethylsilyloxyethyl]-4-[(1R)-1-(3(2-thioxo)thiazolidinyl)carbonylethyl]-2-azetidinone (7) (3S,4S)-3-[(1R)-1-t-Butyldimethylsilyloxyethyl]-4-[(1R)-1-phenylthiocarbonylethyl]-2-azetidinone (8) (3S,4S)-3-[(1R)-1-t-Butyldimethylsilyloxyethyl]-4-[(1R)-1-p-chlorophenylthiocarbonylethyl]-2-azetidinone (9) (3S,4S)-3-[(1R)-1-t-Butyldiphenylsilyloxyethyl]-4-[(1R)-1-p-nitrophenylthiocarbonylethyl]-2-azetidinone

(10) (3S,4S)-3-[(1R)-1-t-Butyldiphenylsilyloxyethyl]-4-[(1R)-1-p-methoxyphenylthiocarbonylethyl]-2-azetidinone

(11) (3S,4S)-3-[(1R)-1-Trimethylsilyloxyethyl]-4-[(1R)-1-phenylthiocarbonylethyl]-2-azetidinone

(12) (3S,4S)-3-[(1R)-1-Trimethylsilyloxyethyl]-4-[(1R)-1-p-chlorophenylthiocarbonylethyl]-2-azetidinone

(13) (3S,4S)-3-[(1R)-1-Triethylsilyloxyethyl]-4-[(1R)-1-phenylthiocarbonylethyl]-2-azetidinone

(14) (3S,4S)-3-[(1R)-1-Triethylsilyloxyethyl]-4-[(1R)-1-p-chlorophenylthiocarbonylethyl]-2-azetidinone

(15) (3S,4S)-3-[(1R)-1-t-Butyldimethylsilyloxyethyl]-4-[(1R)-1-(2-pyridyl)thiocarbonylethyl]-2-azetidinone

(16) (3S,4S)-3-[(1R)-1-t-Butyldimethylsilyloxyethyl]-4-[(1R)-1-(3-pyridyl)thiocarbonylethyl]-2-azetidinone

(17) (3S,4S)-3-[(1R)-1-t-Butyldimethylsilyloxyethyl]-4-[(1R)-1-(4-pyridyl)thiocarbonylethyl]-2-azetidinone

(18) (3S,4S)-3-[(1R)-1-t-Butyldimethylsilyloxyethyl]-4-[(1R)-1-(2pyrimidyl)thiocarbonylethyl]-2-azetidinone

(19) (3S,4S)-3-[(1R)-1-t-Butyldimethylsilyloxyethyl]-4-[(1R)-1-[2-(4,6-dimethyl)pyrimidyl]thiocarbonylethyl]-2-azetidinone

(20) (3S,4S)-3-[(1R)-1-t-Butyldimethylsilyloxyethyl]-4-[(1R)-1-(benzyl)thiocarbonylethyl]-2-azetidinone

(21) (3S,4S)-3-[(1R)-1-t-Butyldimethylsilyloxyethyl]-4-[(1R)-1-(p-methoxybenzyl)thiocarbonylethyl]-2-azetidinone

(22) (3S,4S)-3-[(1R)-1-t-Butyldimethylsilyloxyethyl]-4-[(1R)-1-(2,4-dimethoxybenzyl)thiocarbonylethyl]-2-azetidinone

(23) (3S,4S)-3-[(1R)-1-t-Butyldimethylsilyloxyethyl]-4-[(1R)-1-(p-nitrobenzyl)thiocarbonylethyl]-2-azetidinone

(24) (3S,4S)-3-[(1R)-1-t-Butyldimethylsilyloxyethyl]-4-[(1R)-1-(o-nitrobenzyl)thiocarbonylethyl]-2-azetidinone

(25) (3S,4S)-3-[(1R)-1-t-Butyldimethylsilyloxyethyl]-4-[(1R)-1-(p-chlorobenzyl)thiocarbonylethyl]-2-azetidinone

(26) (3S,4S)-3-[(1R)-1-t-Butyldimethylsilyloxyethyl]-4-[(1R)-1-(p-chlorophenyloxy)carbonylethyl]-2-azetidinone

(27) (3S,4S)-3-[(1R)-1-t-Butyldimethylsilyloxyethyl]-4-[(1R)-1-(2,4-dichlorophenyloxy)carbonylethyl]-2-azetidinone

(28) (3S,4S)-3-[(1R)-1-t-Butyldimethylsilyloxyethyl]-4-[(1R)-1-(2,4,5-trichlorophenyloxy)carbonylethyl]-2-azetidinone

(29) (3S,4S)-3-[(1R)- 1-t-Butyldimethylsilyloxyethyl]-4-[(1R)-1-(p-nitrophenyloxy)carbonylethyl]-2-azetidinone

(30) (3S,4S)-3-[(1R)- 1-t-Butyldimethylsilyloxyethyl]-4-[(1R)-1-(o-nitrophenyloxy)carbonylethyl]-2-azetidinone

(31) (3S,4S)-3-[(1R)-1-t-Butyldimethylsilyloxyethyl]-4-[(1R)-1-(2,4-dinitrophenyloxy)carbonylethyl]-2-azetidinone

(32) (3S,4S)-3-[(1R)-1-t-Butyldimethylsilyloxyethyl]-4-[(1R)-1-(2-pyridyloxy)carbonylethyl]-2-azetidinone

(33) (3S,4S)-3-[(1R)-1-t-Butyldimethylsilyloxyethyl]-4-[(1R)-1-(3-pyridyloxy)carbonylethyl]-2-azetidinone

(34) (3S,4S)-3-[(1R)-1-t-Butyldimethylsilyloxyethyl]-4-[(1R)-1-(4-pyridyloxy)carbonylethyl]-2-azetidinone The representative examples of the acetic ester derivative of the formula (II) are methyl chloroacetate, ethyl chloroacetate, isopropyl chloroacetate, t-butyl chloroacetate, allyl chloroacetate, methyl bromoacetate, ethyl bromoacetate, isopropyl bromoacetate, t-butyl bromoacetate, 2,2,2-trichloroethyl bromoacetate, allyl bromoacetate, 2-methylallyl bromoacetate, benzyl bromoacetate, p-chlorobenzyl bromoacetate, p-nitrobenzyl bromoacetate, o-nitrobenzyl bromoacetate, 2,4-dinitrobenzyl bromoacetate, p-methoxybenzyl bromoacetate, 2,4-dimethoxybenzyl bromoacetate, methyl iodoacetate, t-butyl iodoacetate, benzyl iodoacetate, p-nitrobenzyl iodoacetate, p-methoxybenzyl iodoacetate, benzyl benzenesulfonyloxyacetate, benzyl p-toluenesulfonyloxyacetate, benzyl p-nitrobenzenesulfonyloxyacetate, benzyl p-bromobenzenesulfonyloxyacetate, benzyl methanesulfonyloxyacetate, benzyl ethanesulfonyloxyaetate, benzyl trifluoromethanesulfonyloxyacetate, and the like.

The compounds (III) thus prepared by the present invention are useful as an intermediate for preparing 1β-alkylcarbapenem compounds, for example, the compounds of the formula (V) as described hereinafter, from which the protecting groups are removed to give the final products useful as an antibacterial agent.

The conversion of the intermediate compounds (III) into the carbapenem compounds (V) may be carried out by a known processor example, by treating the compound (III) with a mercaptan compound of the formula (X):

$$R_0\text{—SH} \quad (X)$$

wherein $R_0$ is an organic group, in the presence of a base.

However, if desired, the carbapenem compounds (V) may be prepared directly from the compound (I) without isolating the intermediate compounds (III) as illustrated in the following Reaction Scheme-II.

Reaction Scheme-II

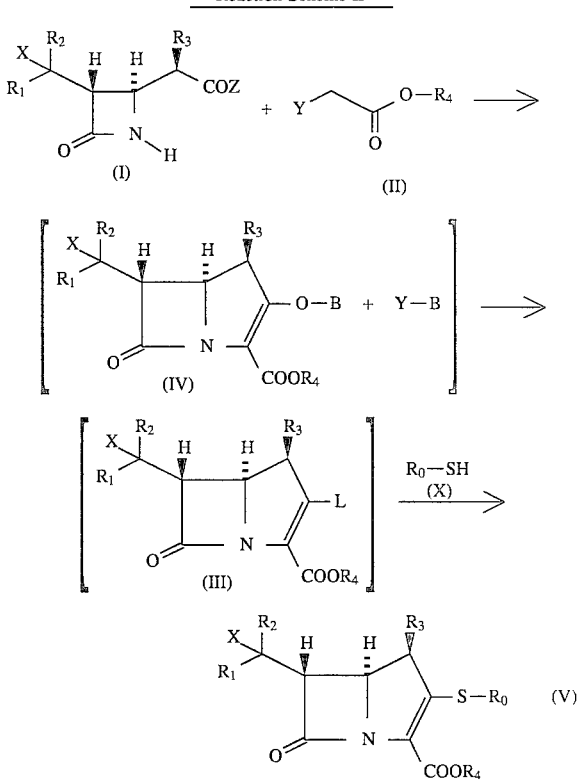

wherein $R_1$, $R_2$, $R_3$, $R_4$, $R_0$, B, X, Y, L and Z are the same as defined above.

This reaction may be carried out by the method disclosed in U.S. Pat. No. 5,310,897.

When the compound (III) is isolated from the reaction system in the above reaction, said compound (III) and the mercaptan compound (X) are reacted in the above mentioned manner to give the carbapenem compound (V).

As mentioned above, the carbapenem compound (III), or if necessary, the carbapenem compound (V) can be obtained from the β-lactam compound (I).

The carbapenem compound (V) thus obtained may be easily converted into the final carbapenem compound of the formula (VI):

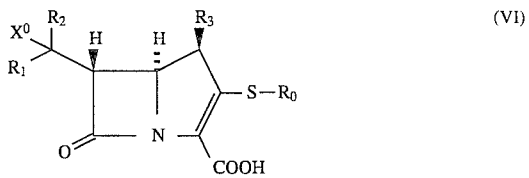

wherein $R_1$, $R_2$, $R_3$ and $R_0$ are the same as defined above, and $X^0$ is hydrogen atom or hydroxy group, by the method disclosed in U.S. Pat. No. 5,310,897.

That is, the compound of the formula (V):

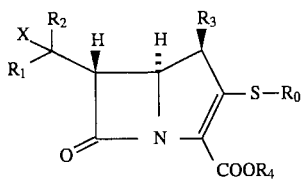

wherein $R_I$, $R_2$, $R_3$, $R_4$, $R_0$ and X are the same as defined above, is subjected to the removal of the protecting group for hydroxy group, the removal of the protecting group for carboxyl group and/or the removal of the protecting group for amino group to give the carbapenem compound (VI) having an antibacterial activity.

The $R_0$ of the 3-substituent, $SR_0$ in the carbapenem compound (V) may be any conventional one, but suitable examples are a substituted or unsubstituted alkyl group having 1 to 10 carbon atoms; a substituted or unsubstituted alkenyl group having 2 to 10 carbon atoms; a cycloalkyl group, an alkylcycloalkyl group, or a cycloalkyl-alkyl group each having 3 to 6 carbon atoms in the cycloalkyl moiety and 1 to 6 carbon atoms in the alkyl moiety; an aryl group such as phenyl; an arylalkyl group wherein the aryl moiety is phenyl and the alkyl moiety is one having 1 to 6 carbon atoms; a heteroaryl group, a heteroarylalkyl group, a heterocycloalkyl group, and these groups may optionally be substituted at least one group selected from amino group, a mono-, di- or tri-alkylamino group having 1 to 4 carbon atoms in the alkyl moiety, hydroxy group, an alkoxy group having 1 to 4 carbon atoms, mercapto group, an alkylthio group having 1 to 4 carbon atoms in the alkyl moiety, an arylthio group such as phenylthio group, sulfamoyl group, amidine group, guanidino group, nitro group, a substituted or unsubstituted carbamoyl group, sulfamoylamino group, a halogen atom such as chlorine, bromine, fluorine, etc., cyano group and carboxyl group. Besides, the above heterocyclic groups such as heteroaryl, heterocycloalkyl contain 1 to 4 heteroatoms selected from oxygen atom, nitrogen atom and sulfur atom, and the alkyl moiety in the above substituents may have 1 to 6 carbon atoms.

The process for preparing carbapenem compounds of the present invention is illustrated in more detail by exemplifying the process for preparing 1β-methylcarbapenem compounds as shown in the following Reaction Scheme-II', that is, in the case of the above Reaction Scheme-II, wherein X is hydrogen atom, $R_I$ is $CH_3$, $R_2$ is a protected hydroxy group and $R_3$ is $CH_3$.

Reaction Scheme-II'

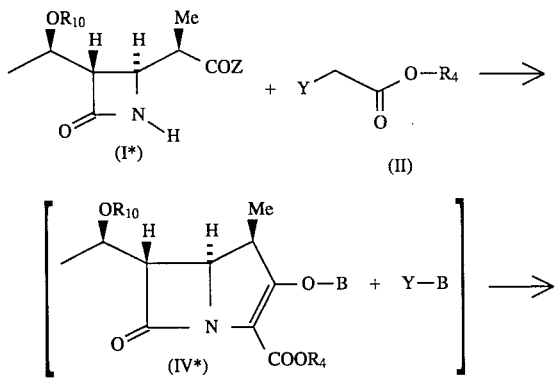

-continued
Reaction Scheme-II'

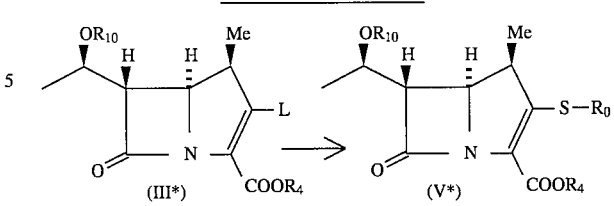

wherein $R_4$, Y, Z, B, L and $R_0$ are the same as defined above, and $R_{10}$ is a protecting group for hydroxy group.

The β-lactam compound of the formula (I*) is subjected successively to the following reactions:

(1) treatment with the acetic acid ester derivative (II) in the presence of a base in an inert solvent;

(2) treatment with an active esterifying agent for hydroxy group; and if necessary, (3) reaction with a mercaptan derivative (X):

$$R_0\text{—SH} \quad\quad\quad (X)$$

wherein $R_0$ is the same as defined above, in the presence of a base, or reaction with a salt of the compound (X) with a base, in the same vessel to give the compound (III*) or the compound (V*).

In the reaction (1), (i) the binding of an acetic acid ester residue to the nitrogen atom of the β-lactam compound (I) and (ii) the binding of the carbonyl group of COZ to the methylene moiety of the acetic acid ester residue (cyclization reaction) may occur simultaneously, or may occur successively to give the enolate (IV*). Besides, under a specific condition, the capture of the released Z residue by the acetic acid ester derivative (II) may also occur simultaneously.

When the reactions (1) and (2) are not carried out in the same vessel, the epimerization of the β-methyl group of the compound of the formula (IV-2*):

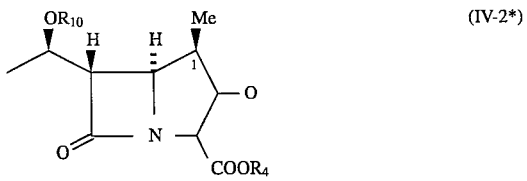

wherein $R_4$ and $R_{10}$ are the same as defined above, which is obtained by subjecting the compound (I*) to the reaction (1) and by the subsequent treatment, may easily occur under various conditions, for example, reaction in the presence of a base, preservation in a solution of high concentration thereof, or preservation in a polar solvent such as acetonitrile, by which the compound (III*) cannot be stereo-selectively prepared in a large scale from the compound (IV-2*) after isolating the compound (IV-2*) from the reaction system. On the contrary, the process of converting the compound (IV*) into the compound (III*) in the same vessel is more advantageous than the process of converting the compound (IV-2*) into the compound (III*) because the former reaction can proceed without epimerization of the 1β-methyl group.

When $R_1$, $R_2$ and X are each different in the compound of the formula (I), for example, when $R_1$ is methyl group, $R_2$ is hydrogen atom and X is a protected hydroxy group, the carbon atom binding to the 3-position of the β-lactam nucleus is also an asymmetric carbon. Thus, the compound of the formula (I) may exist in the form of a stereoisomer other than ones illustrated by the formula (I) due to said asymmetric carbon. All these stereoisomers are simply illustrated by the formula (I), and the present invention also includes these isomers as well.

The present invention is illustrated in detail by the following Examples and Reference Examples, but should not be construed to be limited thereto.

In the present invention, the following abbreviations are used.
TBDMS: t-Butyldimethylsilyl group
TMS: Trimethylsilyl group
Me: Methyl group
Ph: Phenyl group
PNB: p-Nitrobenzyl group
PNZ: p-Nitrobenzyloxycarbonyl group
TES: Triethylsilyl group

EXAMPLE 1

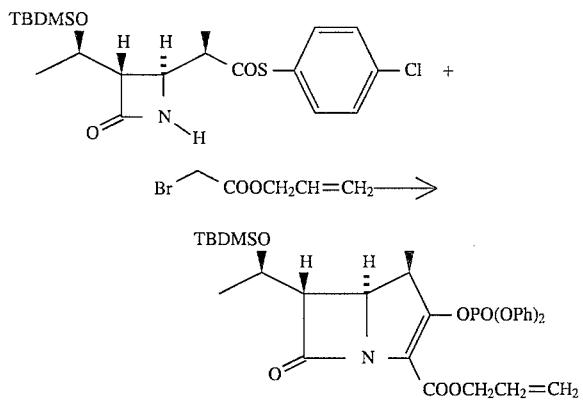

(3S,4S)-3-[(1R)-1-t-Butyldimethylsilyloxyethyl]-4-[(1R)-1-p-chlorophenylthiocarbonylethyl]-2-azetidinone (316 mg, 0.737 mmol) and allyl bromoacetate (315 mg, 1.76 mmol) are dissolved in tetrahydrofuran (4 ml), and the mixture is added dropwise into a suspension of sodium hydride (60% dispersion, 114 mg, 2.85 mmol) in tetrahydrofuran (2 ml) at −35° C., and the mixture is stirred for 30 minutes. To the mixture is added dropwise a solution of diphenyl chlorophosphate (213 mg, 0.793 mmol) in tetrahydrofuran (2 ml), and the mixture is stirred for one hour. The reaction mixture is diluted with ethyl acetate (20 ml), washed several times with brine, dried over a mixed desiccating agent of magnesium sulfate-potassium carbonate (10:1 ), and evaporated to remove the solvent. The residue is purified by silica gel thin layer chromatography to give (4R,5R,6S,8R)-3-diphenylphosphoryloxy-4-methyl-6-(1-t-butyldimethylsilyloxyethyl)-1-azabicyclo[3.2.0]hept-2-en-7-one-2-carboxylic acid allyl ester (334 mg).

IR $^{neat}$ (cm$^{-1}$): 1782, 1731, 1490, 1294, 1189, 970, 837, 777

NMR δ (CDCl$_3$): 0.06 (3Hx2, s), 0.87 (3Hx3, s), 1.18 (3H, d, J=7.3 Hz), 1.23 (3H, d, J=6.0 Hz), 3.24 (1H, dd, J=3.0 and 6.3 Hz), 3.42 (1H, m), 4.14 (1H, dd, J=2.8 and 10.4 Hz), 4.20 (1H, m), 4.65 (2H, d, J=5.6 Hz), 5.40 (2H, m), 5.86 ( 1 H, m), 7.19–7.38 (10H)

EXAMPLE 2

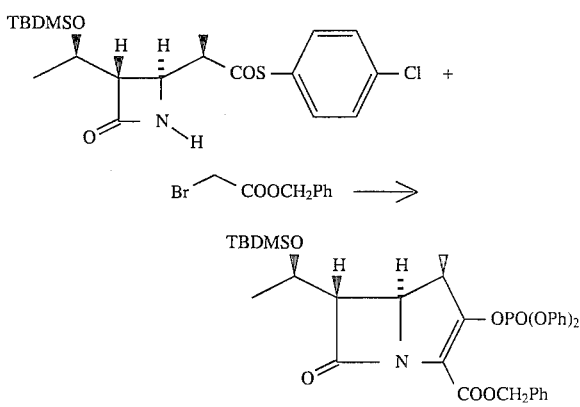

(3S ,4S)-3-[(1R)-1-t-Butyldimethylsilyloxyethyl]-4-[(1R)-1-p-chlorophenylthiocarbonylethyl]-2-azetidinone (467 mg, 1.09 mmol) and benzyl bromoacetate (549 mg, 2.4 mmol) are dissolved in tetrahydrofuran (4 ml), and the mixture is added dropwise into a suspension of sodium hydride (60% dispersion, 157 mg, 3.92 mmol) in tetrahydrofuran (3 ml) at −35° C., and the mixture is stirred for 30 minutes. To the mixture is added dropwise a solution of diphenyl chlorophosphate (307 mg, 1.145 mmol) in tetrahydrofuran (2 ml), and the mixture is stirred for one hour. The reaction mixture is diluted with ethyl acetate (20 ml), washed several times with brine, dried over a mixed desiccating agent of magnesium sulfate-potassium carbonate (10:1 ), and evaporated to remove the solvent. The residue is purified by silica gel thin layer chromatography to give (4R,5R,6S,8R)-3-diphenylphosphoryloxy-4-methyl-6-(1-t-butyldimethylsilyloxyethyl)-1-azabicyclo[3.2.0]hept-2-en-7-one-2-carboxylic acid benzyl ester (410 mg).

IR $^{neat}$ (cm$^{-1}$): 1784, 1729, 1590, 1489, 1189, 970, 834, 778

NMR δ (CDCl$_3$): 0.05 (3H, s), 0.06 (3H, s), 0.85 (3Hx3, s), 1.18 (3H, d, J=7.3 Hz), 1.22 (3H, d, J=6.3 Hz), 3.24 (1H, dd, J=3.0 and 5.9 Hz), 3.44 (1H, m), 4.14 (1H, dd, J=2.8 and 10.4 Hz), 4.21 (1H, m), 5.21 (2H, AB), 7.15–7.38 (15H)

EXAMPLE 3

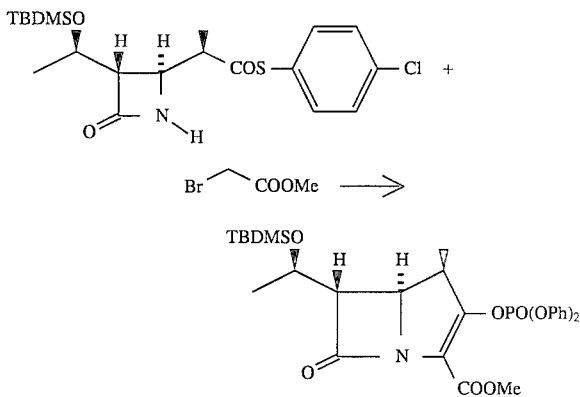

(3S ,4S)-3-[(1R)-1-t-Butyldimethylsilyloxyethyl]-4-[(1R)-1-p-chlorophenylthiocarbonylethyl]-2-azetidinone (389 mg, 0.907 mmol), methyl bromoacetate (303 mg, 1.98 mmol), sodium hydride (60% dispersion, 130 mg, 3.25 mmol) and diphenyl chlorophosphate (254 mg, 0.945 mmol)

are treated in the same manner as in Examples 1 and 2 to give (4R,5R,6S,8R)-3-diphenylphosphoryloxy-4-methyl-6-(1-t-butyldimethylsilyloxyethyl)-1-azabicyclo[3.2.0]hept-2-en-7-one-2-carboxylic acid methyl ester (207 mg).

IR $^{neat}$ (cm$^{-1}$): 1785, 1732, 1489, 1290, 1187, 969, 836, 778

NMR δ (CDCl$_3$): 0.06 (3H×2, s), 0.87 (3H×3, s), 1.18 (3H, d, J=7.3 Hz), 1.23 (3H, d, J=6.3 Hz), 3.24 (1H, dd, J=3.0 and 6.6 Hz), 3.41 (1H, m), 3.69 (3H, s), 4.13 (1H, dd, J=3.0 and 10.2 Hz), 4.20 (1H, m), 7.22–7.38 (10 H)

EXAMPLE 4

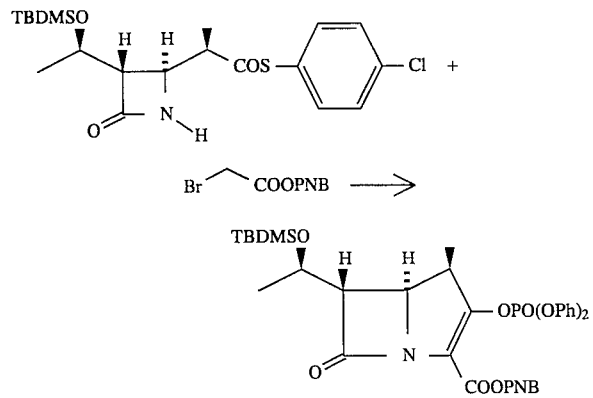

(3S,4S)-3-[(1R)-1-t-Butyldimethylsilyloxyethyl]-4-[(1R)-1-p-chlorophenylthiocarbonylethyl]-2-azetidinone (343 mg, 0.8 mmol), p-nitrobenzyl bromoacetate (482 mg, 1.76 mmol), sodium hydride (60% dispersion, 114 mg, 2.85 mmol) and diphenyl chlorophosphate (236 mg, 0.88 mmol) are treated in the same manner as in Examples 1 and 2 to give (4R,5R,6S,8R)-3-diphenylphosphoryloxy-4-methyl-6-(1-t-butyldimethylsilyloxyethyl)-1-azabicyclo[3.2.0]hept-2-en-7-one-2-carboxylic acid p-nitrobenzyl ester (206 mg).

IR $^{neat}$ (cm$^{-1}$): 1775, 1725, 1630, 1585, 1518, 1482, 1340, 1285, 1185, 1160, 938, 825, 770

NMR δ (CDCl$_3$): 0.06 (3H, s), 0.07 (3H, s), 0.86 (9H, s), 1.20 (3H, d, J=7.9 Hz), 1.23 (3H, d, J=6.3 Hz), 3.29 (1H, dd, J=3.0 and 6.0 Hz), 3.43 (1H, m), 4.22 (2H, m), 5.28 (2H, ABq, J=13.5 Hz), 7.56 (2H, d, J=8.9 Hz), 8.14 (2H, d, J=8.9 Hz)

EXAMPLE 5

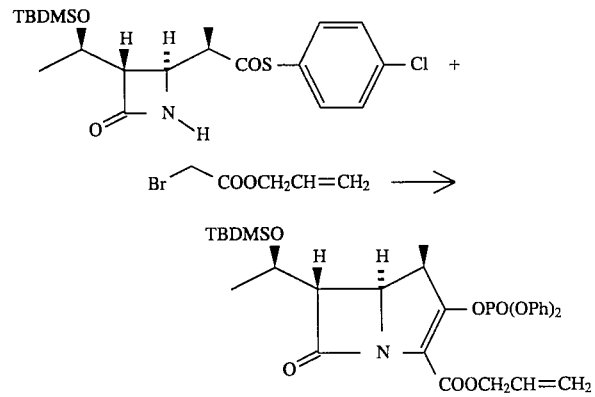

(3S,4S)-3-[(1R)-1-t-Butyldimetylsilyloxyethyl]-4-[(1R)-1-p-chlorophenylthiocarbonylethyl]-2-azetidinone (343 mg, 0.8 mmol) and allyl bromoacetate (304 mg, 1.7 mmol) are dissolved in a mixed solvent of tetrahydrofuran and toluene (1:1, 4 ml), and the mixture is added dropwise into a suspension of sodium hydride (60% dispersion, 100 mg, 2.5 mmol) in a mixed solvent of tetrahydrofuran and toluene (1:1, 2 ml) at −35° C., and the mixture is stirred for 30 minutes. To the mixture is added diphenyl chlorophosphate (215 mg, 0.8 mmol), and the mixture is stirred for one hour. The reaction mixture is treated in the same manner as in Examples 1 and 2 to give (4R,5R,6S,8R)-3-diphenylphosphoryloxy-4- methyl-6-(1-t-butyldimethylsilyloxyethyl)-1-azabicyclo[3.2.0]hept-2-en-7-one-2-carboxylic acid allyl ester (344 mg).

The data of IR spectrum and NMR spectrum of this compound are the same as those of the compound obtained in Example 1.

EXAMPLE 6

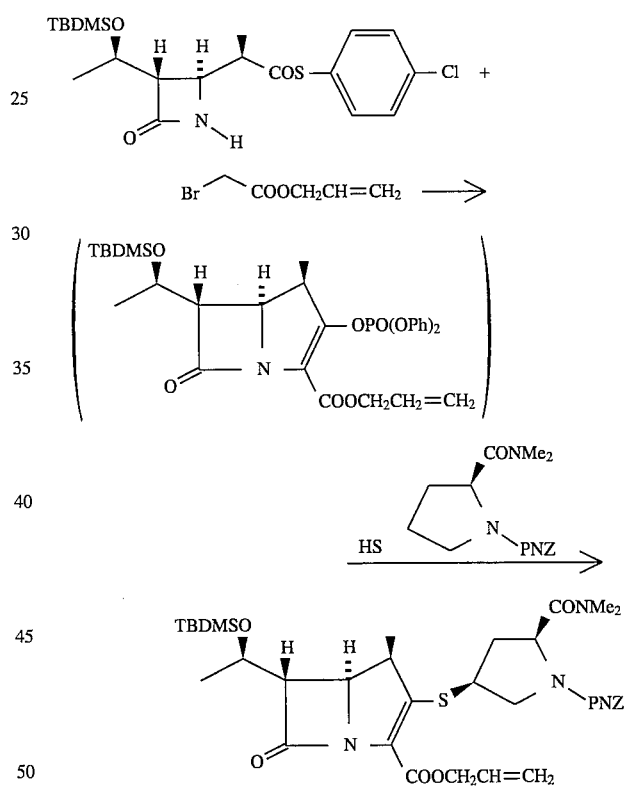

(3S,4S)-3-[(1R)-1-t-Butyldimetylsilyloxyethyl]-4-[(1R)-1-p-chlorophenylthiocarbonylethyl]-2-azetidinone (345 mg, 0.8 mmol), allyl bromoacetate (286 mg, 1.6 mmol), sodium hydride (60% dispersion, 104 mg, 2.6 mmol) and diphenyl chlorophosphate (215 mg, 0.8 mmol) are treated in the same manner as in Example 5. To the resulting (4R,5R,6S,8R)-3-diphenylphosphoryloxy-4-methyl-6-(1-t-butyldimethylsilyloxyethyl)-1-azabicyclo[3.2.0]hept-2-en-7-one-2-carboxylic acid allyl ester are added a solution of [2S,4S]-1-p-nitrobenzyloxycarbonyl-2-dimethylaminocarbonyl-4-mercaptopyrrolidine (282 mg, 0.8 mmol) in acetonitrile (3 ml), and diisopropylethylamine (110 mg, 0.85 mmol) at −20° C., and thereto is added dimethylformamide (3 ml). The mixture is stirred at a temperature from −10° to 0° C. for 12 hours. The reaction mixture is diluted with ethyl acetate (50 ml), washed several times with brine, dried over magnesium sulfate and evaporated to remove the solvent. The residue is purified by silica gel chromatography to give (4R,5S ,6S ,8R,3'S,5'S)-3-[4-(1 -p-nitrobenzyloxycarbonyl-2-dimethylaminocarbonylpyrrolidinyl)thio]-4-methyl-6-(1-t-butyldimethylsilyloxyethyl)-1-azabicyclo[3.2.0]hept-2-en-7-one-2-carboxylic acid allyl ester (95 mg).

IR $^{neat}$ (cm$^{-1}$): 1775, 1710, 1657, 1523, 1345, 1209, 1141, 1110, 983, 836

NMR δ (CDCl$_3$): 0.07–0.08 (3Hx2, s), 0.88 (3Hx3, s), 1.24 (3H,d, J=7.3 Hz), 1.25 (3H, d, J=5.9 Hz), 1.91 (1H, m), 2.72 (1H, m), 2.94 (3Hx2/5, s), 2.98 (3Hx2/5, s), 3.00 (3Hx3/5, s), 3.10 (3Hx3/5, s), 3.20–3.30 (1H, m), 3.31–3.54 (1H, m), 3.70 (1H, m), 4.00–4.26 (3H, m), 4.59–4.81 (3H, m), 5.19 (2Hx2/5, ABq, J=13.5 Hz), 5.22 (2Hx3/5, s), 5.44 (1H, d, J=17.5 Hz), 5.94 (1H, m), 7.44 (lit, d, J=8.6 Hz), 7.52 (1H, d, J=8.6 Hz), 8.20 (1H, d, J=8.6 Hz), 8.23 (1H, d, J=8.6 Hz)

Reference Example 1

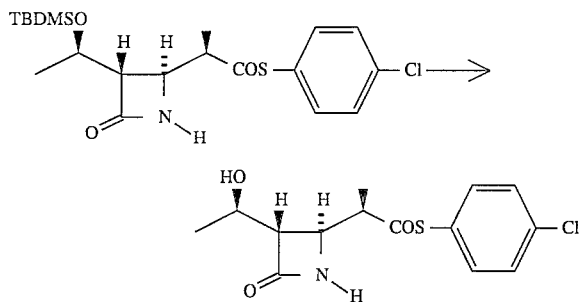

(3S ,4S)-3-[(1R)-1-t-Butyldimethylsilyloxyethyl]-4-[(1R)-1-p-chlorophenylthiocarbonylethyl]-2-azetidinone (1.29 g, 3.0 mmol) is dissolved in toluene (10 ml), and thereto are added methanol (2 ml) and chlorotrimethylsilane (0.1 ml). The mixture is stirred at room temperature overnight. The reaction mixture is diluted with ethyl acetate (50 ml), washed several times with brine, dried over magnesium sulfate, and evaporated to remove the solvent to give (3S, 4S)-3-[(1R)-1-hydroxyethyl]-4-[( 1R)- 1-p-chlorophenylthiocarbonylethyl]-2-azetidinone (627 mg).

IR $^{KBr}$ (cm$^{-1}$): 3329, 1728, 1702, 1476, 1357, 1091, 970, 818

NMR δ (CDCl$_3$): 1.30 (3H, d, J=6.3 Hz), 1.35 (3H, d, J=6.9 Hz), 2.09 (1H, d, J=4.3 Hz), 2.98 (1H, m), 3.09 (1H, dd, J=1.7 and 6.3 Hz), 3.86 (1H, dd, J=2.3 and 6.6 Hz), 4.16 (1H, m), 6.07 (1 H, br.s), 7.32 (2H, d, J=8.6 Hz), 7.40 (2H, d, J=8.6 Hz)

Reference Example 2

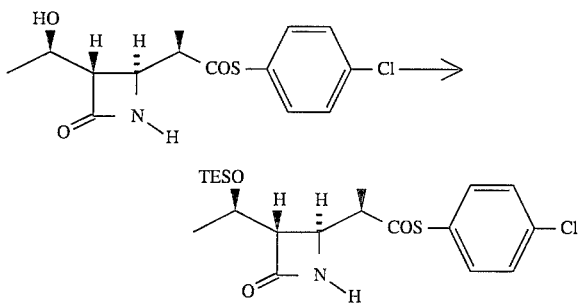

(3S,4S)-3-[(1R)-1-Hydroxyethyl]-4-[(1R)-1-p-chlorophenylthiocarbonylethyl]-2-azetidinone (477 mg, 1.51 mmol) is dissolved in dry N,N-dimethylformamide (3 ml), and thereto are added imidazole (260 mg, 3.79 mmol) and triethylchlorosilane (456 mg, 3.0 mmol), and the mixture is stirred at room temperature for five hours. The reaction solution is diluted with ethyl acetate (30 ml) and washed with water. The aqueous layer is extracted with ethyl acetate (20 ml), and the organic layers are combined, washed twice with brine, dried over sodium sulfate, and evaporated to remove the solvent. The resulting oily residue is purified by silica gel chromatography to give (3S,4S)-3-[(1R)-1-triethylsilyloxyethyl]-4-[(1R)-1-p-chlorophenylthiocarbonyl-ethyl]-2-azetidinone (342 mg).

IR $^{neat}$ (cm$^{-1}$): 1760, 1708, 1478, 1376, 1240, 1145, 1096, 970

NMR δ (CDCl$_3$): 0.60 (2Hx3, q, J=7.9 Hz), 0.95 (3Hx3, t, J=7.6 Hz), 1.21 (3H, d, J=6.3 Hz), 1.32 (3H, d, J=6.9 Hz), 2.99 (1H, m), 3.03 (1H, dd, J=2.1 and 5.0 Hz), 3.92 ( 1 H, dd, J=2.1 and 5.5 Hz), 4.20 ( 1 H, m), 5.99 (1H, br.s), 7.31 (2H, d, J=8.6 Hz), 7.40 (2H, d, J=8.9 Hz)

EXAMPLE 7

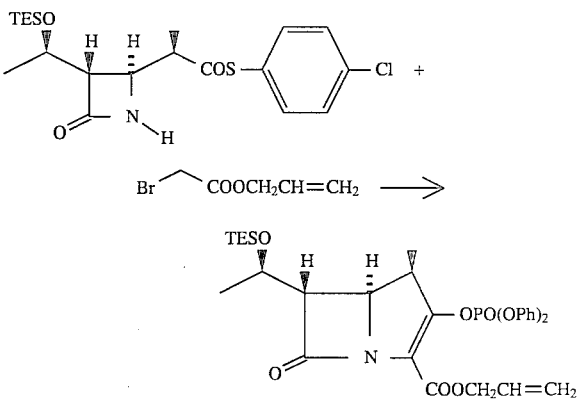

(3S,4S)-3-[(1R)-1-Triethylsilyloxyethyl]-4-[(1R)-1-p-chlorophenylthiocarbonylethyl]-2-azetidinone (170 mg, 0.4 mmol), allyl bromoacetate (152 mg, 0.85 mmol) and sodium hydride (60% dispersion, 50 mg, 1.25 mmol) are treated in the same manner as in Examples 1 and 2 to give (4R,5R, 6S,8R)-3-diphenylphosphoryloxy-4-methyl-6-(1-triethylsilyloxyethyl)-1-azabicyclo[3.2.0]hept-2-en-7-one-2-carboxylic acid allyl ester (60 mg).

IR $^{neat}$ (cm$^{-1}$): 1770, 1746, 1490, 1298, 1189, 970, 747

NMR δ (CDCl$_3$): 0.61 (2Hx3, q, J=7.9 Hz), 0.96 (3Hx3, t, J=7.6 Hz), 1.19 (3H, d, J=7.3 Hz), 1.25 (3H, d, J=6.3 Hz), 3.24 (1H, dd, J=3.0 and 6.6 Hz), 3.42 (1H, m), 4.14 (1H, dd, J=3.0 and 10.2 Hz), 4.20 (1H, m), 4.66 (2H, d, J=5.6 Hz), 5.40 (2H, m), 5.86 (1H, m), 7.21–7.37 (10H)

Reference Example 3

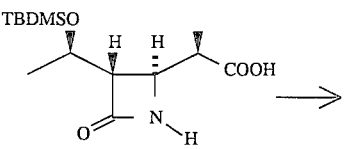

-continued

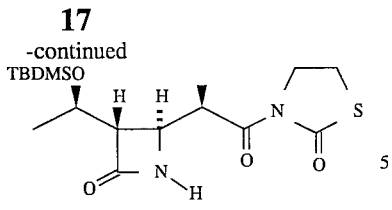

(3S,4S)-3-[(1R)-1-t-Butyldimethylsilyloxyethyl]-4-[(1R)-1carboxyethyl]-2-azetidinone (1.05 g, 3.5 mmol), 2-mercapto-2-thiazoline (417 mg, 3.5 mmol) and 2-chloro-1,3-dimethylimidazolinium chloride (592 mg, 3.5 mmol) are dissolved in methylene chloride (3 ml), and thereto is added pyridine (550 mg, 7.0 mmol) under ice-cooling. The mixture is stirred at room temperature for ten hours, and diluted with methylene chloride (5 ml), and thereto is added water. The organic layer is washed successively with 0.5 N hydrochloric acid, aqueous sodium hydrogen carbonate solution and water, dried over magnesium sulfate, and evaporated to remove the solvent. The residue is purified by silica gel chromatography to give (3S,4S)-3-[(1R)-1-t-butyldimethylsilyloxyethyl]-4-(1R)-1-[3-(2-thioxo)thiazolino]carbonylethyl]-2-azetidinone ( 1.07 g).

IR $^{KBr}$ (cm$^{-1}$): 1763, 1704, 1369, 1280, 1258, 1152, 1058, 835

NMR δ (CDCl$_3$): 0.07 (3Hx2, s), 0.87 (3Hx3, s), 1.21 (3H, d, J=6.3 Hz), 1.26 (3H,d, J=6.9 Hz), 3.04 (1H, dd, J=2.6 and 4.6 Hz), 3.29 (214, dr, J=2.0 and 7.6 Hz), 3.96 (1H, dd, J=2.0 and 4.0 Hz), 4.19 (1H, m), 4.56 (2H, dr, J=1.0 and 7.6 Hzs), 4.96 (1H, m), 5.99 (1H, br.s)

Reference Example 4

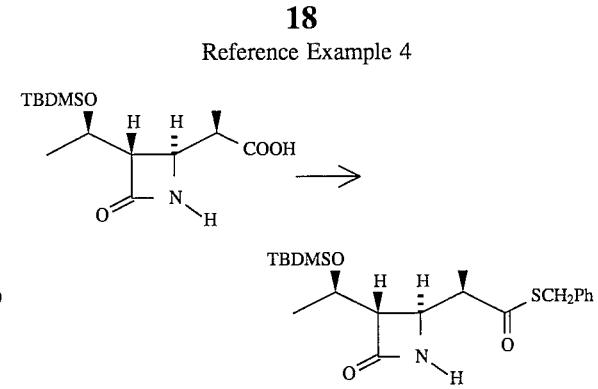

(3S ,4S)-3-[(1R)-1-t-Butyldimethylsilyloxyethyl]-4-[(1R)-1-carboxyethyl]-2-azetidinone (995 mg, 3.3 mmol), benzylmercaptan (409 mg, 3.5 mmol) and 2-chloro-1,3-dimethylimidazolinium chloride (592 mg, 3.5 mmol) are dissolved in methylene chloride (3 ml), and thereto is added dropwise pyridine (550 mg, 7.0 mmol) under ice-cooling. The mixture is stirred at room temperature for 10 hours. The reaction solution is treated in the same manner as in Reference Example 3 to give (3S,4S)-3-[(1R)-1-t-butyldimethylsilyloxyethyl]-4-[(1R)-1-(benzylthiocarbonyl)ethyl]-2-azetidinone (868 mg).

IR $^{neat}$ (cm$^{-1}$): 1764, 1687, 1374, 1255, 1140, 980, 961

NMR δ (CDCl$_3$): 0.06 (3Hx2, s), 0.87 (3Hx3, s), 1.08 (3H, d, J=6.3 Hz), 1.26 (3H, d, J=6.9 Hz), 2.86 (1H, m), 2.98 (1H, dd, J=2.3 and 4.3 Hz), 3.88 (1H, dd, J=2.2 and 5.7 Hz), 4.11 (2H, s), 4.17 (1H, m), 5.84 (1H, br.s), 7.19–7.33 (5H)

EXAMPLE 8

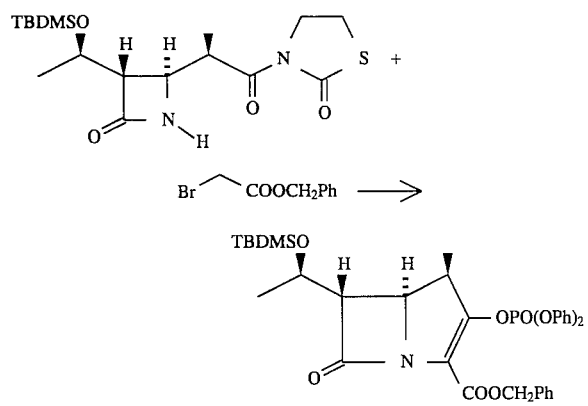

(3S,4S)-3-[(1R)-1-t-Butyldimethylsilyloxyethyl]-4-[(1R)-1-[3-(2-thioxo)thiazolino]carbonylethyl]-2-azetidinone (219 mg, 0.5 mmol), benzyl bromoacetate (137 mg, 0.6 mmol), sodium hydride (60% dispersion, 44 mg, 1.1 mmol), and diphenyl chlorophosphate (135 mg, 0.5 mmol) are treated in the same manner as in Example 2 to give (4R, 5R,6S,8R)-3-diphenylphosphoryloxy-4-methyl-6-(1-t-butyldimethylsilyloxyethyl)-1-azabicyclo[3.2.0]hept-2-en-7-on-2-carboxylic acid benzyl ester (55 mg).

The data of IR spectrum and NMR spectrum of this compound are the same as those of the compound obtained in Example 2.

EXAMPLE 9

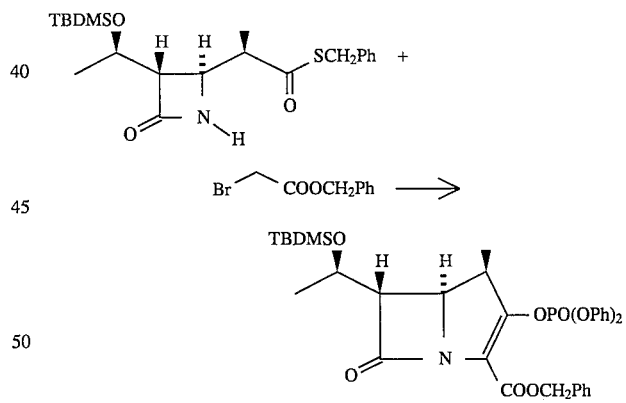

(3S,4S)-3-[(1R)-1-t-Butyldimethylsilyloxyethyl]-4-[(1R)-1-(benzylthiocarbonyl)ethyl]-2-azetidinone (180 mg, 0.406 mmol), benzyl bromoacetate (152 mg, 0.82 mmol), sodium hydride (60% dispersion, 52 mg, 1.3 mmol) and diphenyl chlorophosphate (118 mg, 0.44 mmol) are treated in the same manner as in Example 2 to give (4R,5R,6S,8R)-3-diphenylphsophoryloxy-4-methyl-6-(1-t-butyldimethylsilyloxyethyl)-1azabicyclo[3.2.0]hept-2-en-7-on-2-carboxylic acid benzyl ester (6.5 mg).

The data of IR spectrum and NMR spectrum of this compound are the same as those of the compound obtained in Example 2.

EXAMPLE 10

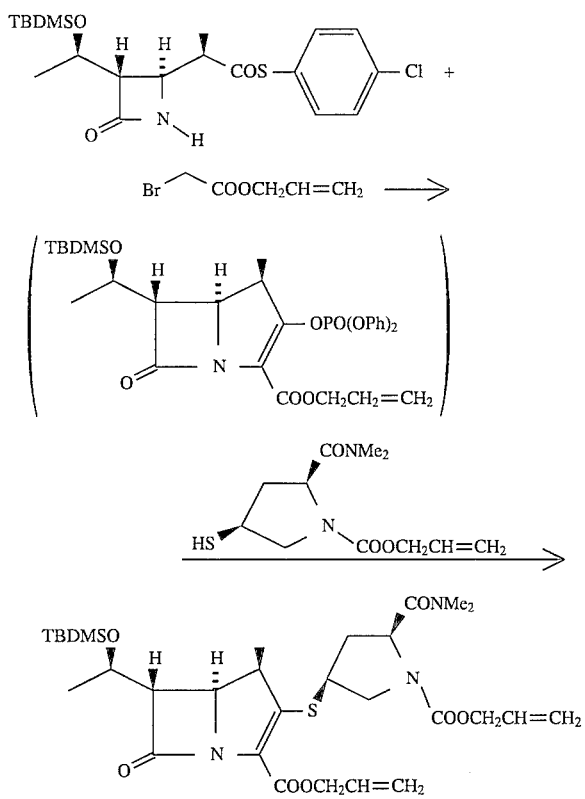

(3S,4S)-3-[(1R)-1-t-Butyldimethylsilyloxyethyl]-4-[(1R)-1-p-chlorophenylthiocarbonylethyl]-2-azetidinone (214 mg, 0.5 mmol) and allyl bromoacetate (197 mg, 0.5 mmol) are dissolved in a mixed solvent of toluene and tetrahydrofuran (8:2, 1.5 ml), and the mixture is added dropwise into a suspension of sodium hydride (60% dispersion, 66 mg, 1.65 mmol) in a mixed solvent of toluene and tetrahydrofuran (8:2, 4.3 g) at a temperature from −35° C. to −40° C., and the mixture is stirred for 1.5 hour. To the mixture is added diphenyl chlorophosphate (148 mg, 0.55 mmol), and the mixture is stirred for two hours. To the resulting (4R,5R,6S,8R)-3-diphenylphosphoryloxy-4-methyl-6-(1-t-butyldimethylsilyloxyethyl)-1-azabicyclo[3.2.0]hept-2-en-7-one-2-carboxylic acid allyl ester are added a solution of [2S,4S]-1-allyloxycarbonyl-2-dimethylaminocarbonyl-4-mercaptopyrrolidine (129 nag, 0.55 mmol) in acetonitrile (0.4 ml) and 1,8-diazabicyclo[5.4.0]undec-7-ene (DBU) (76 mg, 0.5 mmol) at −35° C., and the mixture is stirred at a temperature from −20° C. to 30° C. for one hour. The reaction mixture is diluted with ethyl acetate (50 ml), washed several times with brine, dried over magnesium sulfate and evaporated to remove the solvent. The residue is purified by silica gel chromatography to give (4R,5S,6S,8R, 3'S, 5'S)-3-[4-(1-allyloxycarbonyl-2-dimethylaminocarbonylpyrrolidinyl)thio]-4-methyl-6-(1-t-butyldimethylsilyloxyethyl)-1-azabicyclo[3.2.0]hept-2-en-7-one-2-carboxylic acid allyl ester ( 115 mg).

IR $^{KBr}$ (cm$^{-1}$): 1788, 1704, 1694, 1660, 1553, 1410, 1338, 1209, 1146, 982, 838

NMR δ (CDCl$_3$): 0.08 (3Hx2, s), 0.88 (3Hx3, s), 1.23 (3H, d, J=7.3 Hz), 1.24 (3H, d, J=6.3 Hz), 1.96 (1H, m), 2.65 (1H, m), 2.98 (3H, s), 3.10 (3H, s), 3.21 (1H, m), 3.27 (1H, m), 3.45 (1H, t, J=10.2 Hz), 3.61 (1H, m), 4.01 (1H, dd, J=6.9 and 10.2 Hz), 4.21 (2H, m), 4.54–4.81 (4H+1H, m), 5.16–5.47 (4H, m), 5.85–6.01 (2H, m)

What is claimed is:

1. A process for preparing a carbapenem compound of formula (III):

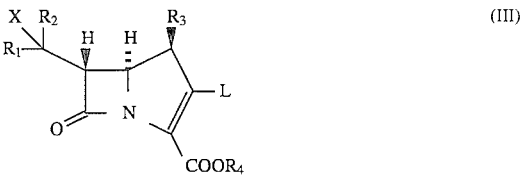

wherein R$_1$ and R$_2$ are the same or different and each is a hydrogen atom or a lower alkyl group, R$_3$ is a lower alkyl group, R$_4$ is a protecting group for a carboxyl group, L is a substituted or unsubstituted arylsulfonyloxy group, a lower alkanesulfonyloxy group, a halogeno-lower alkanesulfonyloxy group, a di-lower alkylphosphoryloxy group, a di-(halogeno-lower alkyl)phosphoryloxy group or a di-(substituted or unsubstituted aryl)phosphoryloxy group, and X is a hydrogen atom or a protected hydroxy group, which consisting of reacting a β-lactam compound of formula (I):

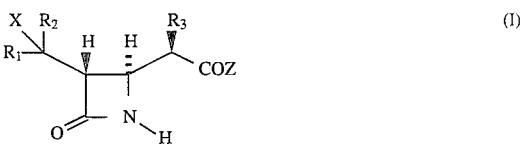

wherein R$_1$, R$_2$, R$_3$ and X are the same as defined above, and COZ is an active ester of a carboxyl group, a substituted or unsubstituted arylthiocarbonyl group, a substituted or unsubstituted heteroarylthiocarbonyl group, a substituted or unsubstituted aralkylthiocarbonyl group, a substituted aryloxycarbonyl group, or a heteroaryloxycarbonyl group, with an excess amount of an acetic acid ester derivative of formula (II) for catching the residue Z$^-$:

wherein Y is a substituted or unsubstituted arylsulfonyloxy group, a lower alkanesulfonyloxy group, a halogeno-lower alkanesulfonyloxy group or a halogen atom, and R$_4$ is the same as defined above, in the presence of a base, followed by treating the product with an active esterifying agent for a hydroxy group.

2. The process according to claim 1, wherein R$_3$ is methyl group.

3. The process according to claim 1, wherein R$_1$ is a hydrogen atom, R$_2$ is a methyl group, R$_3$ is a methyl group, and X is a protected hydroxy group.

4. The process according to claim 1, wherein the molar ratio of the acetic acid ester derivative (II) present in the reaction mixture is 2:1 to 4:1, based on the molar amount of the β-lactam compound (I).

5. The process according to claim 1, wherein the acetic acid ester derivative (II) is reacted with the β-lactam compound (I) at a temperature of from −78° C. to 10° C.

6. The process according to claim 1, wherein the molar ratio of the active esterifying agent for a hydroxy group is 1:1 to 2.5:1, based on the molar amount of the β-lactam compound (I).

7. The process according to claim 1, wherein the product of the reaction of the acetic acid ester derivative (II) and the β-lactam compound (I) is reacted with the active esterifying agent for a hydroxy group at a temperature of −78° C. to 60° C.

8. The process according to claim 1, wherein the product of the reaction of the acetic acid ester derivative (II) and the β-lactam compound (I) is reacted with the active esterifying agent for a hydroxy group at a temperature of −40° C. to 10° C.

9. The process according to claim 1, wherein said base is selected from the group consisting of an alkali metal salt of an amine compound, an alkali metal salt of an alcohol and an alkali metal hydride.

10. The process according to claim 1, wherein said base is sodium hydride.

* * * * *